| United States Patent [19] | [11] Patent Number: 4,816,580 |
| Hansen | [45] Date of Patent: Mar. 28, 1989 |

[54] IMPROVED METHOD FOR PREPARING PENICILLANIC ACID DERIVATIVES

[75] Inventor: Erik T. Hansen, Fredensborg, Denmark

[73] Assignee: Leo Pharmaceutical Products Ltd. A/S, Ballerup, Denmark

[21] Appl. No.: 125,499

[22] PCT Filed: Mar. 24, 1987

[86] PCT No.: PCT/DK87/00030

§ 371 Date: Nov. 24, 1987

§ 102(e) Date: Nov. 24, 1987

[87] PCT Pub. No.: WO87/06230

PCT Pub. Date: Oct. 22, 1987

[30] Foreign Application Priority Data

Apr. 10, 1986 [GB] United Kingdom ............... 8608752
Sep. 24, 1986 [GB] United Kingdom ............... 8623002

[51] Int. Cl.$^4$ ............... C07D 499/00; A61K 31/425

[52] U.S. Cl. ............... 540/310; 514/192; 514/195

[58] Field of Search ............... 540/310; 514/192, 195

[56] References Cited

U.S. PATENT DOCUMENTS 4,714,761 12/1987 Carroll et al. ............... 540/310

OTHER PUBLICATIONS

Hirao et al, *J. Org. Chem.*, 46:3745 ff (1981).

*Primary Examiner*—Nicholas S. Rizzo
*Attorney, Agent, or Firm*—Cushman & Darby & Cushman

[57] ABSTRACT

The present invention relates to a new process for the debromination and/or deiodination of 6,6-dihalo- and 6-monohalopenicillanic acids or derivatives thereof by treatment with dialkyl, trialkyl or diaralkyl phosphite, the desired compounds being obtained in good to excellent yield and in a high state of purity.

11 Claims, No Drawings

IMPROVED METHOD FOR PREPARING PENICILLANIC ACID DERIVATIVES

The present invention relates to a new process for the debromination and/or deiodination of 6,6-dihalo- and 6-monohalopenicillanic acids or derivatives thereof by treatment with a dialkyl, trialkyl or diaralkyl phosphite. The compounds prepared according to the present process have useful pharmacological and chemical properties, for example, as β-lactamase inhibitors or as intermediates for the synthesis of β-lactamase inhibitors and other valuable β-lactams.

More particularly, the invention relates to a new and improved process for the preparation of a 6α-halo compound of the formula I

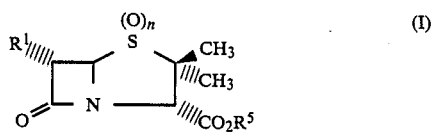

wherein $R^1$ is chloro, bromo or iodo, $R^5$ is hydrogen, a carboxylate salt forming cation, a conventional carboxy protecting group or an ester-forming residue readily hydrolyzable under physiological conditions, and n is an integer of 0 to 2, which comprises treatment of a 6,6-dihalo compound of the formula II

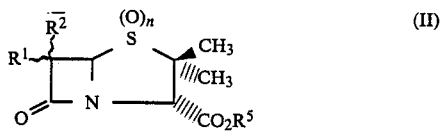

wherein $R^1$, $R^5$ and n are as previously defined and $R^2$ is bromo or iodo, with substantially one molar equivalent of a dialkyl, trialkyl or diaralkyl phosphite.

The same process can also be applied for the preparation of a deshalogenated compound of the formula III

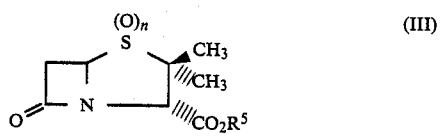

wherein $R^5$ and n are as previously defined, which comprises treatment of a 6,6-dihalo or 6-monohalo compound of the formula IV

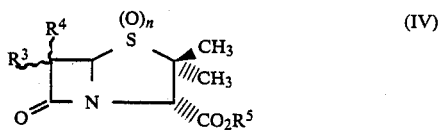

wherein $R^5$ and n are as previously defined and $R^3$ and $R^4$ are each bromo or iodo, or one of $R^3$ and $R^4$ is bromo or iodo and the other is hydrogen, with at least one or at least two molar equivalents, depending on whether one or both of $R^3$ and $R^4$ stand for bromo or iodo, of a dialkyl, trialkyl or diaralkyl phosphite.

Similar dehalogenations have previously been reported, particular attention being paid to the debromination of 6,6-dibromo- and 6-monobromopenicillanic acids or derivatives thereof.

U.S. Pat. No. 4,180,506 describes the catalytic hydrogenation of 6,6-dibromopenicillanic acid in the presence of a palladium-on-carbon catalyst, leading to a mixture of 6α- and 6β-bromopenicillanic acids.

EP No. 0013617 describes the reduction of various esters of 6,6-dibromopenicillanic acid or derivatives thereof with trialkyl or triaryltin hydrides, giving preferentially the 6β-bromo isomers.

Similarly, U.S. Pat. No. 4,397,783 describes the trialkyl- or triaryltin reduction of various 6,6-dihalopenicillanic acid derivatives to provide preferentially the 6β-halo isomers.

EP No. 0092286 describes the preparation of penicillanic acid 1,1-dioxide and derivatives thereof by debromination of 6α-bromo and/or 6,6-dibromopenicillanic acid 1,1-dioxides and derivatives thereof using zinc in association with an acid having a $pK_a$-value of less than 3.5.

EP No. 0129360 and U.S. Pat. No. 4,468,351 describe the debromination of 6-monobromo- and 6,6-dibromopenicillanic acids and various derivatives thereof using a bisulfite salt in a reaction-inert aqueous solvent.

EP Nos. 0138282 and 0139048 describe the debromination of 6,6-dibromo- and 6α-bromopenicillanic acid 1,1-dioxides using magnesium in association with an acid.

However, it is a common feature of the dehalogenation methods of the prior art that they are difficult to apply on a commercial scale, either due to the use of costly and/or dangerous, often toxic reagents and/or the formation of undesired side products difficult to remove and/or necessitating extra purification steps.

It has now surprisingly been found that the dehalogenation of 6,6-dihalo- and 6-monohalopenicillanic acids or derivatives thereof, including the 1,1-dioxides, can readily be performed by treatment with a dialkyl, trialkyl or diaralkyl phosphite in a suitable aqueous solvent at about 0°–100° C., preferably at about 0°–40° C. Hereby, the desired 6α-halopenicillanic or penicillanic acid or derivative thereof is obtained in good to excellent yield and in a high state of purity. Furthermore, it has been shown that the process can readily be scaled up without any loss in the yield or quality of the desired product.

It is therefore a main object of the present invention to provide a simple, economic and industrially applicable process for the preparation of 6α-halopenicillanic and penicillanic acids or derivatives thereof, including the 1,1-dioxides.

In the said phosphite reagents, alkyl stands for straight or branched $C_1$–$C_4$ alkyl, in particular methyl or ethyl, and aralkyl stands for benzyl or phenethyl.

Suitable aqueous solvents include water and mixtures of water with a reaction-inert organic solvent such as ethyl acetate, tetrahydrofuran, acetone or the like.

It is preferred to carry out the process of this invention in the presence of a weak inorganic or organic base, acting as a buffering substance during the dehalogenation reaction. One to four molar equivalents of, for example, sodium or potassium carbonate, or triethylamine are generally well suited for this purpose.

The present method is in particular useful in the preparation of 6α-bromo- and 6α-iodopenicillanic acid and in the preparation of penicillanic acid sulfone.

In formulas (I) to (IV), different meanings of the radical $R^5$ are referred to in general terms which are defined more specifically in the following:

(1) If $R^5$ is a carboxylate salt forming cation, the compounds of formulas (I) to (IV) are pharmaceutically acceptable salts of the compounds of said formulas wherein $R^5$ stand for hydrogen. Pharmaceutically acceptable salts of said compounds include, but are not limited to, those of sodium, potassium and dicyclohexylamine.

(2) The expression "conventional carboxy protecting group" refers to carboxy protecting groups commonly used in the penicillin art and readily removed by catalytic trans-esterification, hydrolysis or hydrogenolysis. In the present invention, allyl and benzyl are used as non-limiting examples of such groups.

(3) Ester-forming residues hydrolyzable under physiological conditions include, but are not limited to, the well-known alkanoyloxyalkyl, alkoxycarbonyloxyalkyl and lactonyl esters groups. As a preferred example of such groups, pivaloyloxymethyl is used in this invention.

The 6,6-dihalo and 6-monohalo starting materials of formulas (II) and (IV) are either known compounds or can be prepared by methods well-known in the art. However, it has been found that 6,6-dihalopenicillanic acids are capable of forming crystalline solvates with dimethyl sulfoxide in a 1:1 molar ratio which are much more stable than the non-solvated acids. These solvates can advantageously be used as starting materials in the present process and form as such a part of this invention.

The present invention is further illustrated by the following, non-limiting Preparations and Examples.

PREPARATION 1

6,6-Dibromopenicillanic acid, dimethyl sulfoxide solvate

Dibromopenicillanic acid (20 g, 22.7 mmol) was dissolved in ethanol (60 ml), and dimethyl sulfoxide (2 ml) was added. The precipitated product was filtered off after 1 hour of agitation at $-10°$ C. and washed with cold ethanol and hexane. Drying afforded 22.65 g (93.0%), $[\alpha]_D^{20} + 175.3°$ (c 0.5, MeOH).

The NMR-spectrum (CDCl$_3$) showed signals at $\delta = 1.54$ (s, 3H), 1.63 (s, 3H), 2.71 (s, 6H), 4.50 (s, 1H), 5.78 (s, 1H), 8.52 (bs, 1H). Tetramethylsilane was used as internal reference.

Anal. Found: C 27.60, H 3.54, Br 36.36, N 3.24, S 14.56%. Calculated for $C_8H_9Br_2NO_3S$, $C_2H_6OS$: C 27.47, H 3.46, Br 36.56, N 3.20, S 14.67%.

PREPARATION 2

6,6-dibromopenicillanic acid, dimethyl sulfoxide solvate

Dibromopenicillanic acid (100 g, 278.51 mmol) was dissolved in isopropanol (300 ml) at 40° C. Dimethyl sulfoxide (25 ml) was added, and the precipitated product was filtered off after 1 hour of agitation at room temperature and 1 hour at $-10°$ C. The product was filtered off and washed with cold isopropanol and hexane. Drying afforded 118.70 g (97.5%); $[\alpha]_D^{20} + 175.0°$ (c 0.5, MeOH).

NMR-spectrum as in Preparation 1.

PREPARATION 3

6,6-Diiodopenicillanic acid, dimethyl sulfoxide solvate 6,6-Diiodopenicilanic acid (11.60 g, 25.6 mmol) was dissolved at about 30° C. in ethanol (15 ml), and to the resulting solution was added dimethyl sulfoxide (2.5 ml) with stirring. The white crystalline product which immediately precipitated was stirred for a further 30 minutes at 0°-5° C. The crystals were collected by filtration, washed with ice-cold ethanol followed by hexane, and dried to to afford 12.46 g (91.6%) of the desired titel compound; $[\alpha]_D^{20} + 195.7°$ (c 0.5, methanol).

The NMR spectrum (CDCl$_3$) showed signals at $\delta = 1.53$ (s, 3H), 1.68 (s, 3H), 2.72 (s, 6H), 4.50 (s, 1H), 5.75 (s, 1H), and 10.33 (bs, 1H). Tetramethylsilane was used a internal reference.

EXAMPLE 1

Dicyclohexylammonium 6α-bromopenicillinate

To a stirred solution of crude 6,6-dibromopenicillanic acid (71.8 g~0.2 mol) and sodium carbonate (42,4 g, 0.4 mol) in water (400 ml) was added at 10° C. diethyl phosphite (28.3 ml, 0.22 mol) during 20 minutes so that the temperature did not exceed 15° C. After the addition was finished, the mixture was stirred for 2 hours and filtered. Ethyl acetate (400 ml) was added, and the pH was adjusted to 2.0 with phosphoric acid (84%). The organic layer was separated and washed with water (200 ml). The apparent pH was with cooling raised to 7.5 with dicyclohexylamine, and the little product crystallized. Filtration and drying gave 56 g (61%) of the title compound, concentration of the other liquor gave a second crop (32.5 g, 35%) of the same quality.

The NMR-spectrum (CDCl$_3$) showed signals at $\delta = 1.0-2.2$ (m, 20H), 1.58 (s, 3H), 1.61 (s, 3H), 2.95 (m, 2H), 4.33 (s, 1H), 4.74 (d, J=1.3 Hz, 1H), 5.33 (d, J=1.3 Hz, 1H), 9.2 (bs, 2H). Tetramethylsilane was used as internal reference).

EXAMPLE 2

Dicyclohexylammonium 6α-iodopenicillanate

By using the same method as described in Example 1, 6,6-diiodopenicillanate was converted to the title product in 80% yield.

The NMR-spectrum (CDCl$_3$) showed signals at $\delta = 1.0-2.0$ (m, 20H), 1.57 (s, 3H), 1.63 (s, 3H), 2.97 (m, 2H), 4.33 (s, 1H), 4.91 (d, J=1.4 Hz, 1H), 5.40 (d, J=1.4 Hz, 1H), 8.20 (bs, 2H). Tetramethylsilane was used as internal reference.

EXAMPLE 3

Dicyclohexylammonium penicillanate 1,1-dioxide

To a mixture of ethyl acetate (75 ml) and water (50 ml) were added 6,6-dibromopenicillanic acid 1,1-dioxide (7.82 g~0.02 mol) and triethylamine (16.6 ml, 0.12 mol), and the mixture was cooled to 5° C. before the addition of diethyl phosphite (6.4 ml, 0.05 mol). Temperature raised immediately to 25° C. After stirring for 45 minutes, the pH of the mixture was adjusted to 1.0 with hydrochloric acid (4N) the organic layer was separated and washed with water (2×25 ml). The apparent pH was adjusted to 7.5 with dicyclohexylamine, and the mixture wad evaporated to yield the crystalline title product (6.7 g, 80%).

The NMR-spectrum (CDCl$_2$) showed signals at δ=1.0–2.3 (m, 20H), 1.50 (s, 3H), 1.62 (s, 3H), 3.00 (m, 2H), 3.38 (d, 2H), 4.10 (s, 1H), 4.60 (t, 1H), 9.1 (bs, 2H). Tetramethylsilane was used as internal reference.

EXAMPLE 4

Allyl penicillanate 1β-oxide

The title product was obtained in 70% yield by the same method as described in Example 3, but using allyl 6α-bromopenicillanate 1β-oxide as starting material and reacting overnight at room temperature.

The NMR-spectrum (CDCl$_3$) showed signals at δ=1.25 (s, 3H), 1.72 (s, 3H), 3.33 (d, 2H), 4.52 (s, 1H), 4.70 (m, 2H), 4.97 (t, 1H), 5.35 (m, 2H), 5.90 (m, 1H). Tetramethylsilane was used as internal reference.

EXAMPLE 5

Allyl penicillanate 1α-oxide

The title product was obtained in 60% yield by the same method as described in Example 3, but using allyl 6β-bromopenicillanate 1α-oxide as starting material and reacting overnight at room temperature.

The NMR-spectrum (CDCl$_3$) showed signals at δ=1.36 (s, 3H), 1.60 (s, 3H), 3.50 (m, 2H), 4.41 (s, 1H), 4.64 (m, 1H), 4.70 (m, 2H), 5.35 (m, 2H), 5.90 (m, 1H). Tetramethylsilane was used as internal reference.

EXAMPLE 6

Dicyclohexylammonium 6α-bromopenicillanate

Using the same procedure as described in Example 1, but reacting with triethyl phosphite, 6,6-dibromopenicillanic acid was converted to the title products in 65% yield.

NMR-spectrum as in Example 1.

EXAMPLE 7

Dicyclohexylammonium 6α-bromopenicillanate 6,6-Dibromopenicilanic acid, DMSO solvate (87.44 g, 0.2 mol) and sodium carbonate (42.4 g, 0.4 mol) were dissolved in water (400 ml), and dimethyl phosphite (20.2 ml, 0.22 mol) was added during 20 minutes keeping the temperature below 10° C. After 2 hours of agitation at room temperature, ethyl acetate (400 ml) was added, and the pH was adjusted to 1.6 with 4N H$_2$SO$_4$. The ethyl acetate phase was separated, washed with water (2×100 ml) and concentrated to about ⅓ of its volume, whereafter hexane (200 ml) was added. Then, the apparent pH of the mixture was adjusted to 7.5 with dicyclohexylamine. The precipitated product was filtered off and dried to give 89.3 g (96.8%) of pure title compound.

NMR-spectrum as in Example 1.

EXAMPLE 8

Dicyclohexylammonium 6α-chloropenicillanate

To a stirred solution of 6-chloro-6-iodopenicillanic acid (1.44 g, 4 mmol) and sodium carbonate (0.84 g, 8 mmol) in water 10 ml) was added dropwise at 0°–5° C. diethyl phosphite (0.58 ml, 4.4 mmol). After the addition was finished, the mixture was stirred at room temperature for 3.5 hours. Ethyl acetate (20 ml) was added, and the apparent pH of the mixture was adjusted to 2.0 by addition of 4N hydrochloric acid. After separation of the layers, the aqueous phase was reextracted with ethyl acetate (20 ml), and the combined organic phases washed with water, dried (MgSO$_4$) and evaporated in vacuo. The residual oil was dissolved in ether (10 ml) and treated with dicyclohexylamine (0.8 ml, 4 mmol) to precipitate a crystaline product. After cooling in iced water, the crystals were collected by filtration, washed with cold ether and dried to give 1.44 g (86%) of the title compound as white crystals; [α]$_D^{20}$+142.9° (c 0.5, methanol).

The NMR spectrum (CDCl$_3$) showed signals at δ=1.0–2.2 (m, 20H), 1.60 (s, 3H), 1.66 (s, 3H), 3.00 (m, 2H), 4.32 (s, 1H), 4.69 (d, J=1.3 Hz, 1H), 5.25 (d, J=1.3 Hz, 1H), and 9.0 (bs, 2H). Tetramethylsilane was used as internal reference.

Anal. Found: C 57.65, H 8.04, Cl 8.40, N 6.75 (s, 7.63%. Calculated for C$_{20}$H$_{33}$ClN$_2$O$_3$S: C 57.61, H 7.98, Cl 8.50, N 6.72, S 7.63%.

EXAMPLE 9

Sodium penicillanate 1,1-dioxide

To a solution of allyl 6,6-dibromopenicillanate 1,1-dioxide (4.31 g, 10 mmol) and triethylamine (1.4 ml, 10 mmol) in ethyl acetate (50 ml) was added water (5 ml) and sodium bicarbonate (2.52 g, 30 mmol). The resulting suspension was heated to 40° C. with stirring, and diethyl phosphite (3.2 ml, 25 mmol) was added dropwise during 5 minutes. After stirring at 40° C. for 4 hours, the mixture was poured onto iced water (25 ml). The organic layer was separated, washed with water and brine, dried over MgSO$_4$ and filtered. To the filtrate was added 100 mg of tetrabis(triphenylphosphine)palladium and 200 mg of triphenylphosphine, and the stirred mixture was treated with a 1M solution of sodium 2-ethylhexanoate in ethyl acetate (10 ml). After stirring for 2 hours, the precipitate was collected by filtration washed with ethyl acetate and dried to give 2.22 g (87%) of the title compound as off-white crystals.

The NMR spectrum (D$_2$O, 4.66 ppm) showed signals at δ=1.42 (s, 3H), 1.55 (s, 3H), 3.38 (dd, J=16 Hz, J=1.9 Hz, 1H), 3.60 (dd, J=16 Hz, J=4.1 Hz, H), 4.17 (s, 1H) and 4.95 (dd, J=1.9 Hz, J=4.1 Hz, 1H).

EXAMPLE 10

Pivaloyloxymethyl 6α-bromopenicillanate

To a solution of pivaloyloxymethyl 6,6-dibromopenicillanate (1.18 g, 2.5 mmol) in ethyl (25 ml) was added water (2.5 ml), sodium bicarbonate (0.63 g, 7.5 mmol) and triethylamine (0.35 ml, 2.5 mmol). The resulting mixture was treated with diethyl phosphite (0.35 ml, 2.75 mmol) and stirred for 2 hours at room temperature. Insoluble material was removed by filtration and washed with ethyl acetate. The organic phase of the filtrate was separated, washed with water, dried (MgSO$_4$) and evaporated at reduced pressure. The oily residue crystallized from diisopropyl ether to give 0.79 g (80%) of the title compound as white crystals; mp. 79°–80° C.

Anal. Found: C 42.66, H 5.15, Br 20.31, N 3.53, S 8.12%. Calculated for C$_{14}$H$_{20}$BrNO$_5$S: C 42.65, H 5.11, Br 20.27, N 3.55, S 8.13%.

EXAMPLE 11

Benzyl 6α-iodopenicillanate

By the same procedure as described in Example 10, but substituting benzyl 6,6-diiodopenicillanate for the pivaloyloxymethyl 6,6-dibromopenicillanate, the title compound was obtained as a colourless oil in 73% yield.

The NMR spectrum (CDCl$_3$) showed signals at δ=1.38 (s, 3H), 1.60 (s, 3H), 4.55 (s, 1H), 4.97 (d, J=1.5 Hz, 1H), 5.18 (s, 2H), 5.46 (d, J=1.5 Hz, 1H) and 7.35 (s, 5H). Tetramethylsilane was used as internal reference.

EXAMPLE 12

Sodium penicillanate 1,1-dioxide

To a 18° C. solution of 6,6-dibromopenicillanic acid 1,1-dioxide (19.55 g, 50 mmol) and sodium bicarbonate (25.2 g, 300 mmol) in 100 ml of water was added diethyl phosphite (16.1 ml, 125 mmol) over 10 minutes, whereby the temperature raised to 35° C. After 4 hours at 40° C. the reaction mixture was cooled to 5° C.

Ethyl acetate (200 ml) was added, and pH was adjusted to 1.5 with hydrochloric acid (4N), the layers were separated, and the ethyl acetate was washed with aqueous saturated CaCl$_2$ (25 ml) and dried with MgSO$_4$.

The apparent pH was adjusted to 7.4 with a sodium 2-ethylhexanoate (2N) solution in ethyl acetate. The mixture was allowed to crystallize for 2 hours, then filtered, washed with ethyl acetate and hexane. Drying afforded 9.78 g (76.5%) of the title compound.

NMR as in Example 9.

What we claim is:

1. A process for the preparation of a compound of the formula I

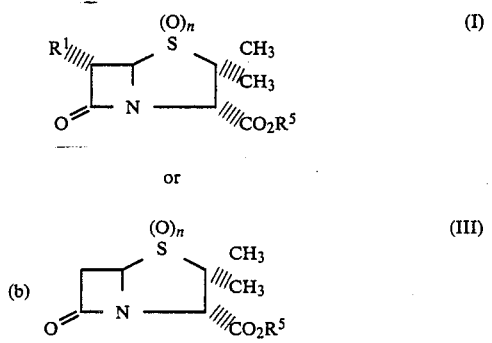

wherein R$^1$ is chloro, bromo or iodo, R$^5$ is hydrogen, a carboxylate salt forming cation, a carboxy protecting group or a residue readily hydrolyzable under physiological conditions, and n is an integer of 0 to 2, which comprises treatment of a compound of the formula

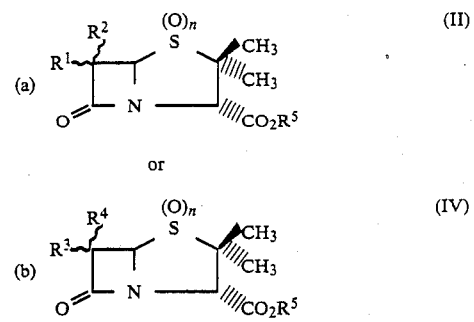

wherein R$^1$, R$^5$ and n are as previously defined, R$^2$, R$^3$ and R$^4$ are each bromo or iodo, or one of R$^3$ and R$^4$ is bromo or iodo and the other is hydrogen, with (a) substantially one molar equivalent or (b) at least one or at least two molar equivalents, depending on whether one or both of R$^3$ and R$^4$ stand for bromo or iodo, of a dialkyl, trialkyl or diaralkyl phosphite in a suitable aqueous solvent and in the presence of one to four molar equivalents of a weakly basic buffering substance at about 0°–100° C.

2. A process according to claim 1, wherein alkyl stands for C$_1$–C$_4$ alkyl.

3. A process according to claim 2, wherein the suitable aqueous solvent is water or a mixture of water and ethyl acetate.

4. A process according to claim 3, wherein the weakly basic buffering substance is selected from the group consisting of sodium/potassium bicarbonate, sodium/potassium carbonate and triethylamine.

5. A process according to claim 4, wherein R$^5$ is hydrogen or a carboxylate salt forming cation.

6. A process according to claim 5, wherein R$^1$ and R$^2$ are bromo or iodo and n is 0.

7. A process according to claim 6, wherein the starting material is a dimethyl sulfoxide solvate.

8. A process according to claim 6, wherein the prepared compound is dicyclohexylammonium 6α-bromopenicillanate.

9. A process according to claim 5, wherein R$^3$ and R$^4$ are bromo and n is 2.

10. A process according to claim 9, wherein the prepared compound is penicillanic acid 1,1-dioxide or a pharmaceutically acceptable salt thereof.

11. A process according to claim 6 wherein the temperature is about 0°–40° C. and the C$_1$–C$_4$ alkyl is methyl or ethyl.

* * * * *